US009452065B1

(12) United States Patent
Lawson

(10) Patent No.: US 9,452,065 B1
(45) Date of Patent: Sep. 27, 2016

(54) SACROILIAC JOINT EXPOSURE, FUSION, AND DEBRIDEMENT

(71) Applicant: Robert Charles Hill, San Francisco, CA (US)

(72) Inventor: Kevin Jon Lawson, Gaylord, MI (US)

(*) Notice: Subject to any disclaimer, the term of this patent is extended or adjusted under 35 U.S.C. 154(b) by 433 days.

(21) Appl. No.: 13/998,889

(22) Filed: Dec. 18, 2013

(51) Int. Cl.
A61F 2/44 (2006.01)
A61F 2/46 (2006.01)

(52) U.S. Cl.
CPC ............ *A61F 2/4611* (2013.01); *A61F 2/4455* (2013.01)

(58) Field of Classification Search
CPC ............... A61B 17/7055; A61F 2002/30995; A61F 2002/30622; A61F 2/46; A61F 2/4611; A61F 2/4455; A61F 2/30988
See application file for complete search history.

(56) References Cited

U.S. PATENT DOCUMENTS

| 6,224,603 | B1* | 5/2001 | Marino | A61B 17/1739 606/79 |
| 6,427,698 | B1* | 8/2002 | Yoon | A61B 17/58 128/898 |
| 8,348,950 | B2* | 1/2013 | Assell | A61B 17/1617 606/79 |
| 8,852,241 | B2* | 10/2014 | Datta | A61B 17/7055 606/246 |
| 8,882,818 | B1* | 11/2014 | Vestgaarden | A61B 17/68 128/898 |
| 9,066,734 | B2* | 6/2015 | Schoenefeld | A61B 17/1757 |
| 9,119,732 | B2* | 9/2015 | Schifano | A61F 2/4611 |
| 2006/0054171 | A1* | 3/2006 | Dall | A61B 17/1664 128/898 |
| 2013/0123850 | A1* | 5/2013 | Schoenefeld | A61B 17/7055 606/248 |
| 2014/0031935 | A1* | 1/2014 | Donner | A61F 2/4455 623/17.11 |
| 2014/0200618 | A1* | 7/2014 | Donner | A61B 17/1757 606/281 |
| 2015/0012051 | A1* | 1/2015 | Warren | A61B 17/8685 606/310 |
| 2015/0190149 | A1* | 7/2015 | Assell | A61B 17/1671 606/80 |
| 2015/0250611 | A1* | 9/2015 | Schifano | A61F 2/447 623/17.16 |
| 2015/0250612 | A1* | 9/2015 | Schifano | A61F 2/447 623/17.16 |
| 2015/0342753 | A1* | 12/2015 | Donner | A61B 17/1757 623/18.11 |

FOREIGN PATENT DOCUMENTS

WO WO 2013134670 A1 * 9/2013 ............... A61F 2/28

* cited by examiner

*Primary Examiner* — Lynnsy Summitt
(74) *Attorney, Agent, or Firm* — Robert Charles Hill

(57) ABSTRACT

A surgical method for exposure of the sacroiliac joint using a posterior approach begins with a longitudinal incision over the posterior iliac crest, centered on the posterior iliac spine. Holes which will be used to repair the iliac osteotomy are made obliquely from the medial to lateral to cross the plane of exposure. A cut through the bone is made lateral to the drill holes and centered over the sacroiliac complex with the aid of fluoroscope or radiograph imaging. The medial part of the iliac crest is freed from the back of the sacrum and displaced medially for the sacroiliac joint complex to be inspected, debrided, or curettaged for fusion. The closure and subsequent healing are facilitated by the predrilled oblique holes. These are used to re-attach the medial iliac bone to the remaining lateral ilium.

8 Claims, 4 Drawing Sheets

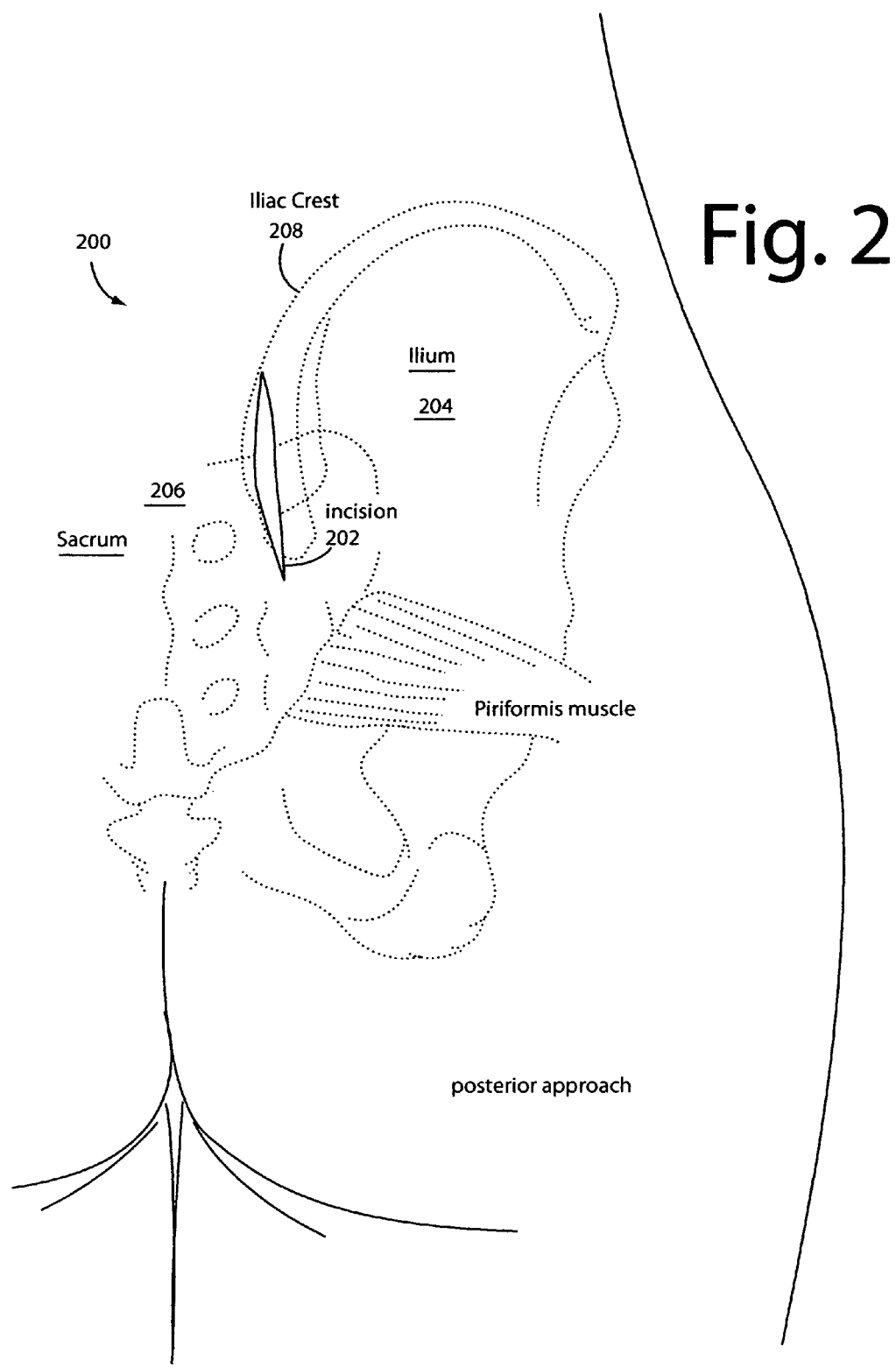

SACROILIAC JOINT EXPOSURE, FUSION, AND DEBRIDEMENT

BACKGROUND OF THE INVENTION

1. Field of the Invention

The present invention relates to medical and surgical methods and devices for sacroiliac joint exposure, fusion, and debridement methods and the reliable restoration of nearby tissues.

2. Description of Related Art

The human body has two sacroiliac joints in the pelvis. In between them is the sacrum which supports the spine at the fifth lumbar vertebrae. So one joint is on the left and the other is close by on the right. The outside of each sacroiliac joint meets and is overlapped by an ilium on each side of the pelvis. The ilium is the uppermost and largest bone of the pelvis. All of these bones are held together by strong ligaments.

Transosseous, medial posterior and anterior exposures of the sacroiliac joint are conventional and each has its shortcomings. For example, these all can cause wide injuries in varying degrees to the soft tissues and bones adjacent to the joint that will consequently interfere with complete healing and restoration of function.

A conventional, and typical posterior technique was described this way in *Canale & Beaty: Campbell's Operative Orthopaedics*, 12th ed. Copyright © 2012 Mosby, An Imprint of Elsevier, Sacroiliac Joint, Posterior Approach to the Sacroiliac Joint Technique 1-74:

Make an incision along the lateral lip of the posterior third of the iliac crest to the posterior superior spine.

Deepen the dissection down to the crest, separate the lumbodorsal fascia from it, detach and reflect medially the aponeurosis of the sacrospinalis muscle together with the periosteum, and expose the posterior margin of the sacroiliac joint. This exposure is ample for extraarticular fusion.

To expose the articular surfaces of the joint for drainage or intraarticular fusion, continue the skin incision laterally and distally 5 to 8 cm from the posterior superior spine. Split the gluteus maximus muscle in line with its fibers, or incise its origin on the iliac crest, the aponeurosis of the sacrospinalis, and the sacrum, and reflect it laterally and distally to expose the posterior aspect of the ilium. Branches of the inferior gluteal nerve and artery may be present.

To expose more of the ilium, reflect the gluteus medius anterolaterally. The gluteus medius cannot be reflected very far anteriorly because of the presence of the superior gluteal nerve and artery.

With an osteotome, remove a full-thickness section of the ilium 1.5 to 2 cm wide, beginning at its posterior border between the posterior superior and posterior inferior spines and proceeding laterally and slightly cephalad for 4 to 5 cm. The inferior border of this section roughly parallels the superior border of the greater sciatic notch. Exposure of the joint is limited by the size of the section removed.

In another conventional, but anterior approach, by Avila: with the patient supine, make a 10 to 12 cm incision 1.5 cm proximal to and parallel with the iliac crest, beginning at the anterosuperior iliac spine. Dissect distally to the iliac crest and detach the abdominal muscles from it without disturbing the origin of the gluteal muscles. Incise the periosteum and strip the iliacus muscle subperiosteally, following the medial surface of the ilium medially and slightly distally. Retract the iliacus medially and complete the stripping by hand with the gloved finger covered with gauze. Proceed as far as the lateral attachments of the anterior sacroiliac ligament; detach them and palpate the joint. To expose the anterior aspect of the joint, extend the incision further posteriorly in the intermuscular plane along the iliac crest.

What is needed is a method for reliable exposure of the posterior inferior portion of the sacroiliac joint that minimizes injury to the surrounding ligaments and muscles. A mechanism of healing is necessary that is reliable and easily stabilized. Anatomic orientation should also be included to help the surgeon recover the correct positioning relative to the oblique sacroiliac joint complex.

SUMMARY OF THE INVENTION

Briefly, a surgical method embodiment of the present invention comprises positioning the patient prone on a radiolucent surgical support table. Fluoroscopy or radiographs are used to confirm the pelvis, and lateral outline of the sacrum and Sacroiliac joint complex. A longitudinal incision is planned over the posterior iliac crest, centered on the posterior iliac spine. An incision is made down the iliac crest to expose the deep fascia. Holes which will be used to repair the iliac osteotomy are made obliquely from the medial to lateral to cross the plane of exposure. A series of holes or a bur cut are made lateral to the previous drill holes and centered over the sacroiliac complex with the aid of fluoroscope or radiograph imaging. The cut is parallel to the main axis of the spine and extends from the distal to the proximal away from the sciatic notch. The cut is guided by the imaging. An osteotome or side cutting burr is used to complete the osteotomy. The medial part of the iliac crest is freed from the back of the sacrum and displaced medially. This then exposes the back of the sacrum and sacroiliac joint complex for inspection, debridement, and curettage for fusion. Harvested bone or allograft can be applied respectively to the prepared fusion surfaces on the sacrum and ilium. The exposure within the joint may be used to guide a targeting device for sacroiliac joint fixation prior to closure. Such exposure of the sacroiliac joint can also be used advantageously to place a fusion device inside the joint proper. The closure and subsequent healing are facilitated by the predrilled oblique holes. These are used to re-attach the medial iliac bone to the remaining lateral ilium. Thereafter, the closure of the remaining soft tissues and skin are routine.

The above and still further objects, features, and advantages of the present invention will become apparent upon consideration of the following detailed description of specific embodiments thereof, especially when taken in conjunction with the accompanying drawings.

BRIEF DESCRIPTION OF THE DRAWINGS

FIG. 2 is a posterior view of an incision that is made over the right posterior of the pelvis of a patient undergoing the surgical method of FIG. 1.

3C and 3D especially show how during closure the detached medial part of the iliac crest is accurately repositioned and stabilized.

DETAILED DESCRIPTION OF THE INVENTION

The posterior approach to exposing the sacroiliac joint is generally considered safe and simple because it does not endanger vital structures. This approach has been widely used to treat disruptions of the sacroiliac joint, fractures of the ilium near the joint, and infections of the sacroiliac joint and surrounding bones.

Surgical method embodiments of the present invention use a much smaller, vertical incision and iliac osteotomy (pelvis bone cutting) to expose the sacroiliac joint underneath.

Figure 1:
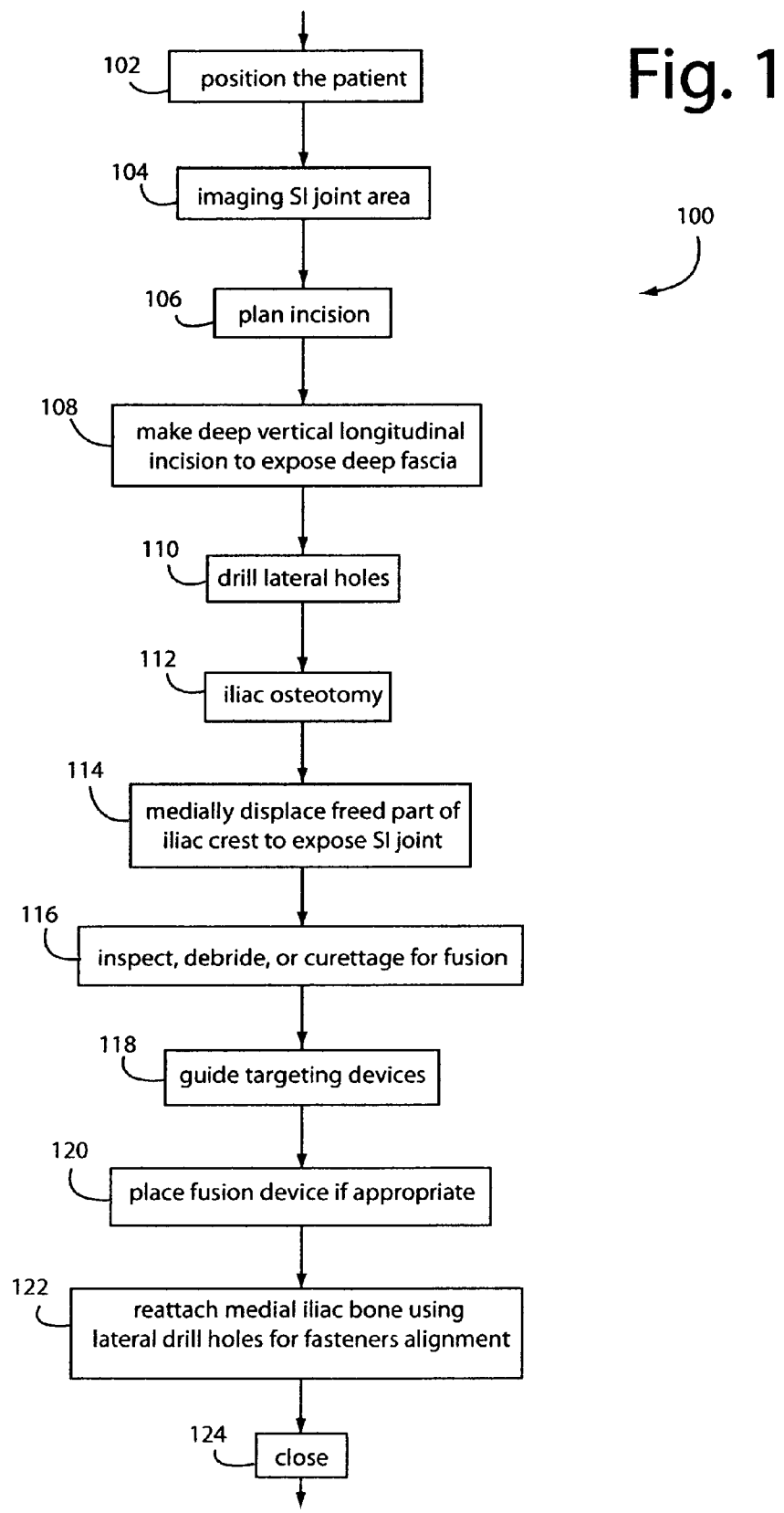
FIG. 1 is a flowchart diagram of a surgical method embodiment of the present invention for posterior exposure of the sacroiliac joint and surgical closure.

FIG. 1 illustrates a surgical method embodiment of the present invention for sacroiliac joint exposure, fusion, and debridement methods and the reliable restoration of nearby tissues, and such is referred to herein by the general reference numeral 100.

Method begins in a step 102 by positioning the patient prone on a radiolucent surgical support table. Fluoroscopy or radiographs are used in a step 104 to confirm the pelvis, and lateral outline of the sacrum and Sacroiliac joint complex. In a step 106, a longitudinal incision is planned over the posterior iliac crest, centered on the posterior iliac spine. An incision is made in a step 108 down the iliac crest to expose the deep fascia.

In a step 110, guide holes are drilled obliquely from the medial to lateral to cross the plane of exposure. These guide holes will be used later for placing fasteners, and thereby improve the reliability of the repair of the iliac osteotomy when closing.

An iliac osteotomy proceeds in a step 112 by making a series of holes or a burr cut which are lateral to the guide holes. The osteotomy is centered over the sacroiliac complex with the aid of fluoroscope or radiograph imaging. The iliac osteotomic cutting proceeds from the distal to the proximal, away from the sciatic notch, with visual guidance provided by the imaging.

An osteotome or side cutting burr is used to complete the osteotomy. A medial edge of the iliac crest covering the SI joint area of the sacrum is thus freed without its being completely separated from the body. It can then be moved out of the way in a step 114 to one side over toward the middle of the body to expose the SI joint.

The surgical incision is minimal and effectively straight down vertically into the sacroiliac joint and longitudinally through the overlapping part of the ilium using osteotomy.

In a step 116, the back of the sacrum and sacroiliac joint complex are thus exposed for inspection, debridement, and curettage for fusion. Harvested bone or allograft can be applied respectively to prepared fusion surfaces on the sacrum and ilium.

In a step 118, the exposure within the sacroiliac joint can be used to guide a targeting device for sacroiliac joint fixation prior to closure. Such exposure of the sacroiliac joint can also be used in a step 120 to advantageously to place a fusion device inside the joint proper. The closure and subsequent healing are facilitated by the predrilled oblique holes. In a step 122, fasteners are inserted into the predrilled holes to re-attach the medial iliac bone to the remaining lateral ilium. Thereafter in a step 124, the closure of the remaining soft tissues and skin are routine.

FIG. 2 represents a posterior approach 200 for the right-side. An incision 202 is made in the overlapping area of the ilium 204 and the sacrum 206 down through the deep fascia to the iliac crest 208. The left side of the sacrum 206 would be approached similarly.

FIGS. 3A-3D represent a posterior view the pelvis 300 of a patient. Such is more or less symmetrical on the left and the right. Here, we have chosen to illustrate an embodiment that addresses the right side of the patient. The surgical treatment of the left side would be about the same.

In this instance on the right, the iliac spine 302 joins a medial part 304 of the iliac crest 306 which overlaps the sacrum 308. Beneath this overlap lies the sacroiliac joint (318 in FIG. 3B).

Figure 3A:
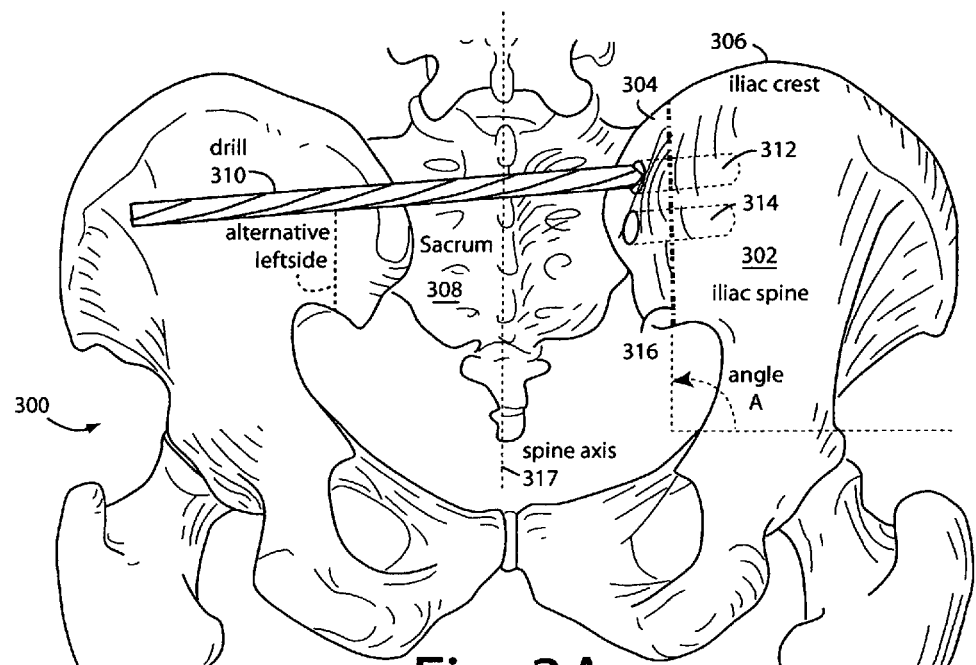
FIGS. 3A-3D are a time series of posterior view diagrams of the exposure of a patient's right sacroiliac joint using the incision of FIG. 2 and the surgical method of FIG. 1. FIGS.

With reference now to FIG. 3A, surgical method 100 (FIG. 1) uses a drill 310 to laterally drill two oblique holes 312 and 314 through the medial part 304 of the ilium right and into the iliac wing. These holes will be used later by fasteners to help properly align a subsequent re-attachment of the medial part 304 to the iliac spine 302.

A line 316 represents the track of bone cutting done in the iliac osteotomy step 112 (FIG. 1). Such track 316 is generally parallel to the main axis 317 of the spine, represented by "Angle-A", and can vary ±10° without adverse effect. The cut can be normal, straight down from the bone surface, or angled from one side to the other to cause a beveled edge on each cut surface.

Figure 3B:
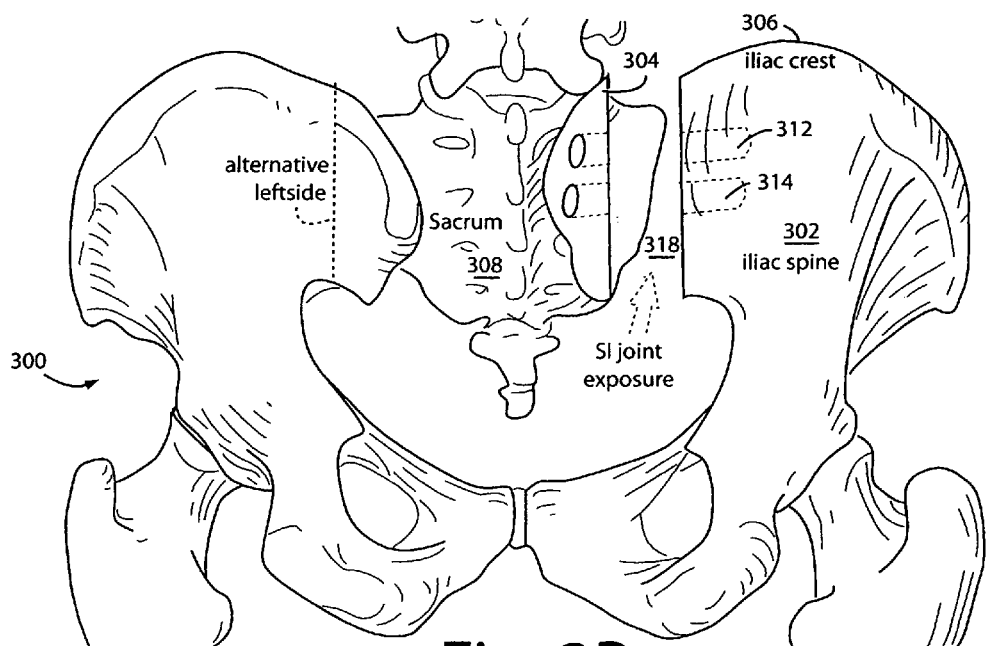

In FIG. 3B, the now freed medial part 304 is pushed medially away from the remaining iliac spine 302, as in step 114. This then exposes the sacroiliac joint 318 for inspection, debridement, bone fusion, etc.

Figure 3C:
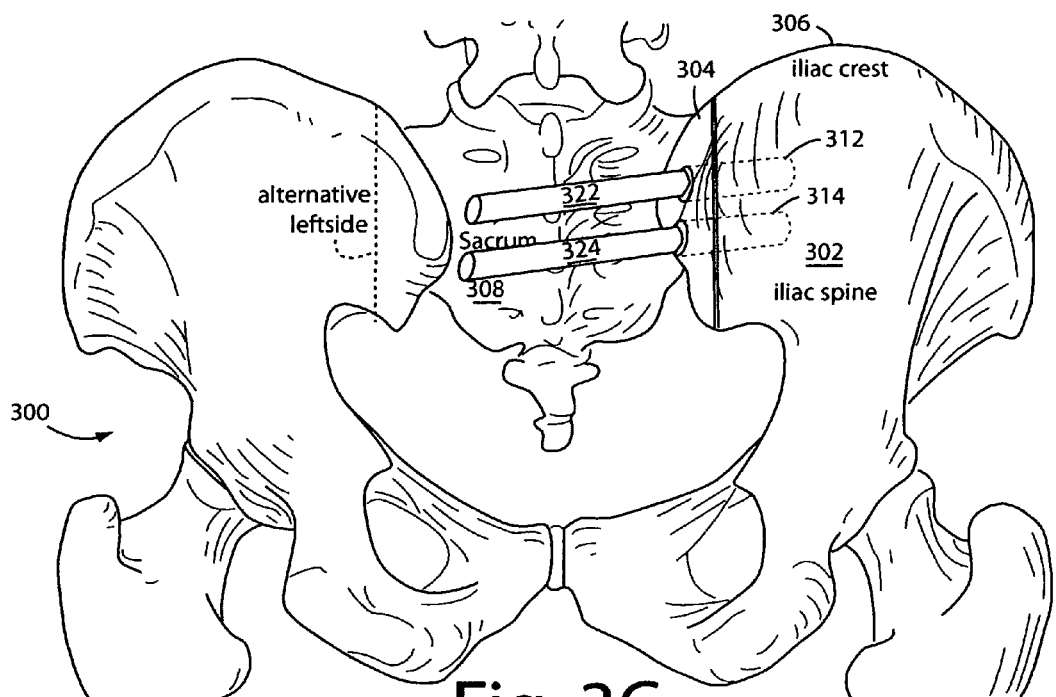
Figure 3D:
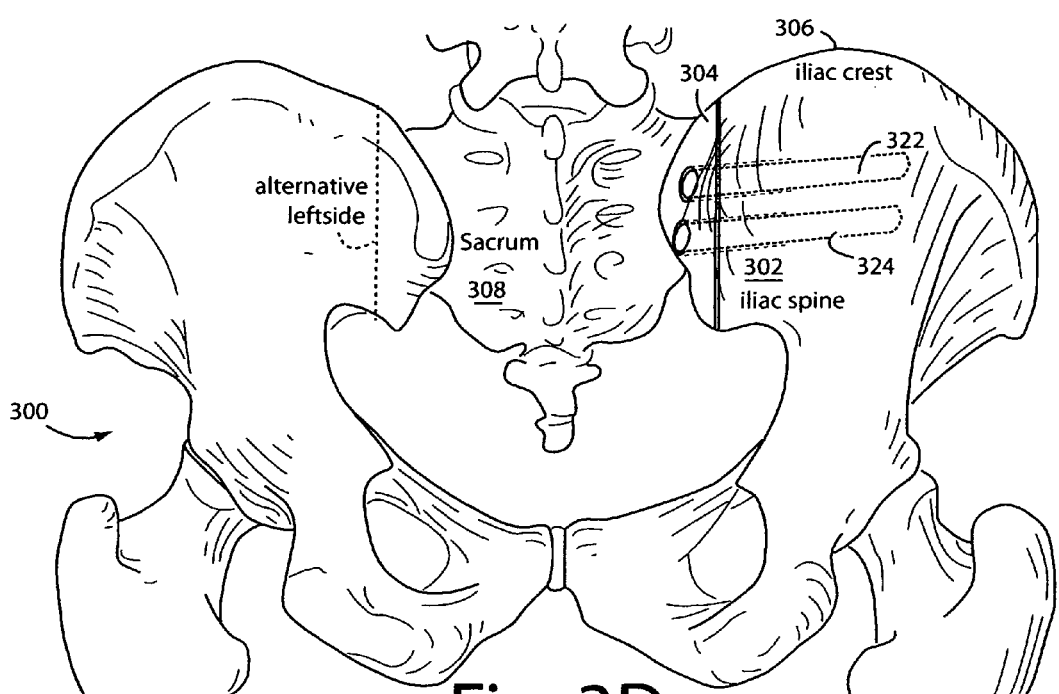

In FIGS. 3C and 3D, the procedures needed on the sacroiliac joint 318 are completed and the free medial part 304 is moved laterally back into its original position on the iliac spine 302. As in step 122, a pair of fasteners 322 and 324 are inserted into holes 312 and 314 to accurately align, secure, and stabilize medial part 304 in its original position on iliac spine 302.

Fasteners 322 and 324 can comprise any number and manner of screws, pins, wires, staples, or other conventional surgical components for holding and stabilizing bones for post-operative healing.

Although particular embodiments of the present invention have been described and illustrated, such was not intended to limit the invention. Modifications and changes will no doubt become apparent to those skilled in the art, and it was intended that the invention only be limited by the scope of the appended claims.

The invention claimed is:

1. A method for surgical exposure of a sacroiliac joint in a human patient, comprising:
    making a deep, vertical, longitudinal incision in the posterior of the patient to expose deep fascia and an iliac crest of an ilium directly overlying the sacroiliac joints;
    predrilling at least one hole for a fastener medially from the iliac crest laterally into a main body of the ilium through an area that is later subject to iliac osteotomy;
    using iliac osteotomic cutting of a medial portion of the iliac crest overhanging the sacroiliac joint to free it so it can thereafter be moved medially out of the way to expose the corresponding underlying sacroiliac joint;
    using an access of the sacroiliac joint thus afforded by such exposure of the sacroiliac joint to complete a predetermined surgical procedure;

restoring said medial portion of the iliac crest to its original position overhanging the sacroiliac joint and securing it to the ilium using a fasteners installed in said predrilled hole; and closing the incision;

wherein, surgical invasion of the patient's body to expose the sacroiliac joint is thereby minimized, and the iliac osteotomy is precisely restored as original.

2. The method for the surgical exposure of a sacroiliac joint of claim 1, further comprises:

inspecting the sacroiliac joint as part of said predetermined surgical procedure.

3. The method for the surgical exposure of a sacroiliac joint of claim 1, further comprises:

debriding the sacroiliac joint as part of said predetermined surgical procedure.

4. The method for the surgical exposure of a sacroiliac joint of claim 1, further comprises:

bone fusing the sacroiliac joint as part of said predetermined surgical procedure.

5. The method for the surgical exposure of a sacroiliac joint of claim 4, further comprises:

preparing bone fusion surfaces on respective parts of a sacrum and ilium in the sacroiliac joint; and applying bone or allograft to said prepared fusion surfaces.

6. The method for the surgical exposure of a sacroiliac joint of claim 4, further comprises:

using the exposure within the sacroiliac joint to guide targeting devices for sacroiliac joint fixation prior to closing the incision.

7. The method for the surgical exposure of a sacroiliac joint of claim 1, further comprises:

restricting the iliac osteotomic cutting of said medial portion of the iliac crest to a line generally parallel to the longitudinal axis of the patient's spine, and not exceeding ±10° of parallel angle.

8. The method for the surgical exposure of a sacroiliac joint of claim 1, further comprises:

tilting the iliac osteotomic cutting of said medial portion of the iliac crest to cause a beveled edge in the resulting bone cut.

* * * * *